(12) United States Patent
Kelly et al.

(10) Patent No.: US 12,266,103 B2
(45) Date of Patent: Apr. 1, 2025

(54) CONDITION DIAGNOSIS USING USER DEVICE

(71) Applicant: Lenovo (Singapore) Pte. Ltd., Singapore (SG)

(72) Inventors: Sean C. Kelly, Wake Forest, NC (US); Koji Kawakita, Yokohama (JP)

(73) Assignee: Lenovo (Singapore) Pte. Ltd., Singapore (SG)

( * ) Notice: Subject to any disclaimer, the term of this patent is extended or adjusted under 35 U.S.C. 154(b) by 461 days.

(21) Appl. No.: 17/855,048

(22) Filed: Jun. 30, 2022

(65) Prior Publication Data

US 2024/0005482 A1    Jan. 4, 2024

(51) Int. Cl.
| | |
|---|---|
| *G06T 7/00* | (2017.01) |
| *A61B 5/00* | (2006.01) |
| *G06T 7/514* | (2017.01) |
| *G06T 7/60* | (2017.01) |
| *G06V 10/82* | (2022.01) |
| *G16H 50/20* | (2018.01) |
| *G16H 80/00* | (2018.01) |
| *H04L 65/403* | (2022.01) |

(52) U.S. Cl.
CPC .......... *G06T 7/0012* (2013.01); *A61B 5/0075* (2013.01); *A61B 5/0077* (2013.01); *G06T 7/514* (2017.01); *G06T 7/60* (2013.01); *G06V 10/82* (2022.01); *G16H 50/20* (2018.01); *G16H 80/00* (2018.01); *H04L 65/403* (2013.01); *G06T 2207/10024* (2013.01); *G06T 2207/10048* (2013.01); *G06T 2207/20081* (2013.01); *G06T 2207/20084* (2013.01); *G06T 2207/30004* (2013.01); *G06T 2207/30196* (2013.01)

(58) Field of Classification Search
None
See application file for complete search history.

(56) References Cited

U.S. PATENT DOCUMENTS

2013/0331664 A1* 12/2013 Gilad-Gilor ........... A61B 5/741
                                                    600/407
2019/0198167 A1*  6/2019 Durlach ............... A61B 5/6892

* cited by examiner

*Primary Examiner* — Dov Popovici
(74) *Attorney, Agent, or Firm* — FERENCE & ASSOCIATES LLC

(57) ABSTRACT

One embodiment provides a method, the method including: obtaining, using at least one sensor of an information handling device facilitating a video conference, at least one image of a portion of a user of the information handling device participating in the video conference, wherein at least one participant in the video conference is located remotely with respect to the user; identifying, using an image diagnosis system, a condition of the portion of the user by analyzing the at least one image of the portion of the user; and transmitting, using the image diagnosis system, the condition to the at least one participant. Other aspects are claimed and described.

20 Claims, 3 Drawing Sheets

CONDITION DIAGNOSIS USING USER DEVICE

BACKGROUND

With the increase in people and users becoming geographically diverse, an increase in communications over different communication mediums has also been observed. Additionally, the features, functions, and reliability of the communication mediums has increased. One common increasingly popular communication medium is the use of video calls or conferences. This allows video of participants to be transmitted to other participants in the call or conference. Also, video or images of other things, such as an environment of the user, a desktop or objects on a display device of a user, and/or the like, can be transmitted to other participants. While video conferencing is popular in a work environment, it has also become increasingly popular for other uses. For example, users are increasingly using video conferencing in personal calls. As another example, meetings or appointments that are traditionally conducted in-person have employed the use of video conferencing, for example, doctor or other medical professional appointments.

BRIEF SUMMARY

In summary, one aspect provides a method, the method including: obtaining, using at least one sensor of an information handling device facilitating a video conference, at least one image of a portion of a user of the information handling device participating in the video conference, wherein at least one participant in the video conference is located remotely with respect to the user; identifying, using an image diagnosis system, a condition of the portion of the user by analyzing the at least one image of the portion of the user; and transmitting, using the image diagnosis system, the condition to the at least one participant.

Another aspect provides a system, the system including: an information handling device including at least one sensor; a processor operatively coupled to the information handling device; a memory device that stores instructions that, when executed by the processor, causes the system to: obtain, using the at least one sensor of the information handling device that is facilitating a video conference, at least one image of a portion of a user of the information handling device participating in the video conference, wherein at least one participant in the video conference is located remotely with respect to the user; identify, using an image diagnosis system, a condition of the portion of the user by analyzing the at least one image of the portion of the user; and transmit, using the image diagnosis system, the condition to the at least one participant.

A further aspect provides a product, the product including: a computer-readable storage device that stores executable code that, when executed by a processor, causes the product to: obtain, using at least one sensor of an information handling device facilitating a video conference, at least one image of a portion of a user of the information handling device participating in the video conference, wherein at least one participant in the video conference is located remotely with respect to the user; identify, using an image diagnosis system, a condition of the portion of the user by analyzing the at least one image of the portion of the user; and transmit, using the image diagnosis system, the condition to the at least one participant.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
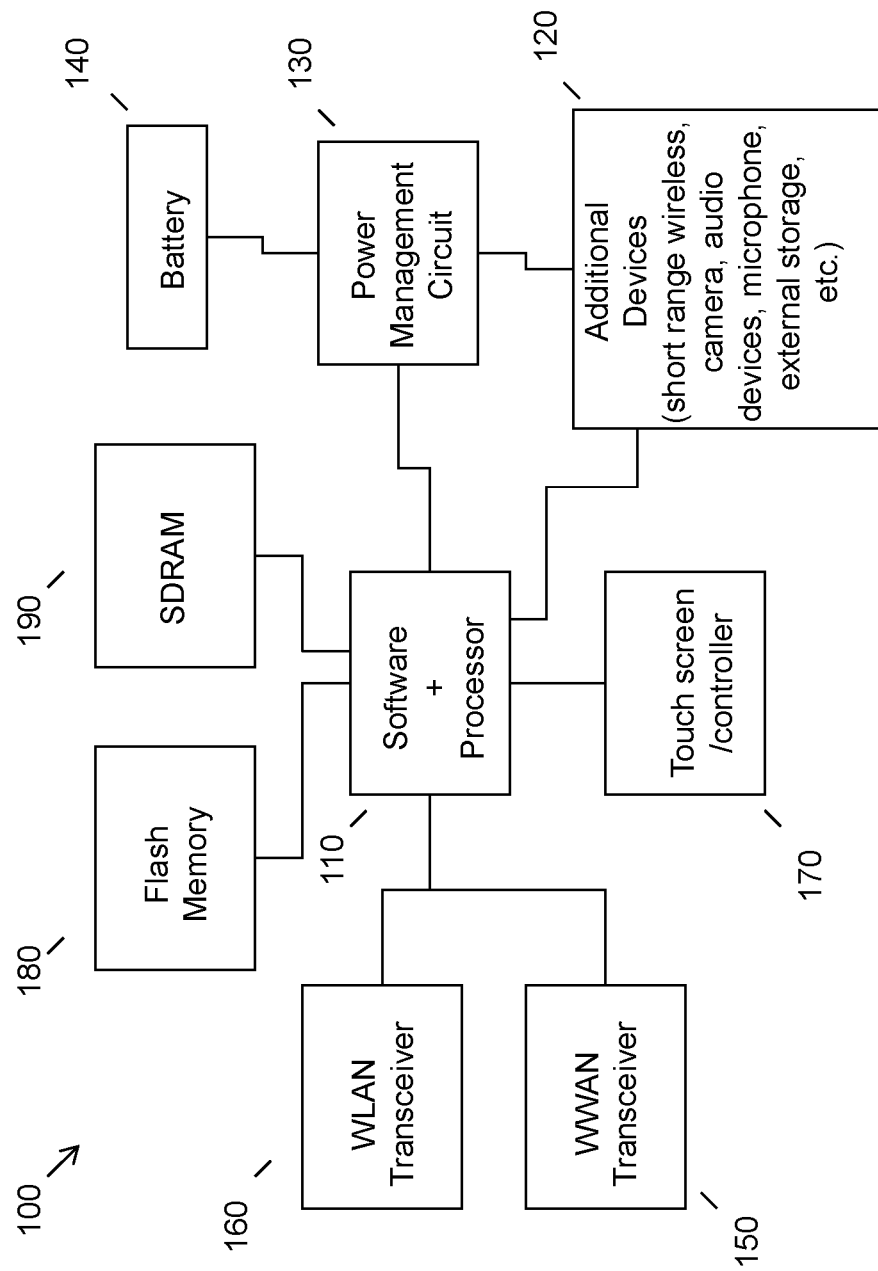
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

While it may be beneficial to be able to conduct appointments over video conferencing or other non-traditional techniques, as compared to traditional in-person appointments, due to a reduction in the amount of time spent driving, the ability of a person who is unable to easily move to stay in a single location, a reduction of the amount of time spent in a waiting room, the reduction in the amount of contact between people generally, and the like. However, video conferences do not provide all of the same benefits as traditional in-person appointments. For example, while video conferences do allow doctors or other health professionals to visually see the patient, the images produced on a typical user device may not be of great enough quality to allow a person to see minor nuances, different color shading, depth, and/or the like.

While some conditions do not need high image quality, some conditions may be undiagnosable or unable to be correctly diagnosed without the ability to gain more information regarding the condition. For example, dermatological conditions, eye conditions, bruising, and/or the like, may be difficult to diagnose correctly without being able to ascertain more information regarding the condition. In these situations, the only solution is to have a physical visit with the medical professional or other person performing the diagnosis. There are some imaging devices that are able to ascertain the details and quality that would be necessary for assisting in diagnosing a condition. However, these are high quality and expensive imaging devices that are not generally available to a typical user without going to a medical facility or imaging facility. Thus, the only way for a person to get an accurate diagnosis requires the person to go to a different facility.

Accordingly, the described system and method provides a technique for identifying a condition of a portion of a user from images captured by an information handling device and transmitting the condition to a remote participant. The image diagnosis system obtains at least one image of a portion of a user using an information handling device. The information handling device is being used to facilitate a video conference with at least one remote participant. The images may include color images and near infrared images. Thus, the information handling device may include multiple image sensors that allow for the capture of different types of images.

Once the images are obtained, an image diagnosis system identifies a condition of the portion of the user by analyzing the image(s) of the portion of the user. Analyzing the images may include using a neural network, machine-learning model, or other type of learning algorithm that can be trained and used to predict conditions. To make the identification, the system may measure different characteristics of the image. For example, the system can measure a spectral reflectance of the near infrared image which can provide additional information regarding color, depth, shape, position, and/or the like of the portion of the user. As another example, the system can measure a size of the portion of the user. Once the system makes an identification of a condition, the condition is transmitted to the remote participant.

Therefore, a system provides a technical improvement over traditional methods for identifying conditions of user, by allowing for the identification of conditions using video or images. The described system and method utilize image sensors contained within a traditional user device, thereby not requiring the use of a high-quality medical grade imaging device. This allows a user to use a traditional user device (e.g., smart phone, laptop computer, personal computer, smart watch, etc.) to conduct video conferences with medical professionals and get quality images that will allow the medical professional to diagnose conditions of the user without requiring the user to go to a different facility. Thus, the user can stay in a single location without having to drive to a facility, come into contact with other people, spend time waiting for an appointment, and/or the like.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, input/output (I/O) ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use serial advanced technology attachment (SATA) or peripheral component interconnect (PCI) or low pin count (LPC). Common interfaces, for example, include secure digital input/output (SDIO) and inter-integrated circuit (I2C).

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply basic input/output system (BIOS) like functionality and dynamic random-access memory (DRAM) memory.

System 100 typically includes one or more of a wireless wide area network (WWAN) transceiver 150 and a wireless local area network (WLAN) transceiver 160 for connecting to various networks, such as telecommunications networks and wireless Internet devices, e.g., access points. Additionally, devices 120 are commonly included, e.g., a wireless communication device, external storage, etc. System 100 often includes a touch screen 170 for data input and display/rendering. System 100 also typically includes various memory devices, for example flash memory 180 and synchronous dynamic random-access memory (SDRAM) 190.

Figure 2:
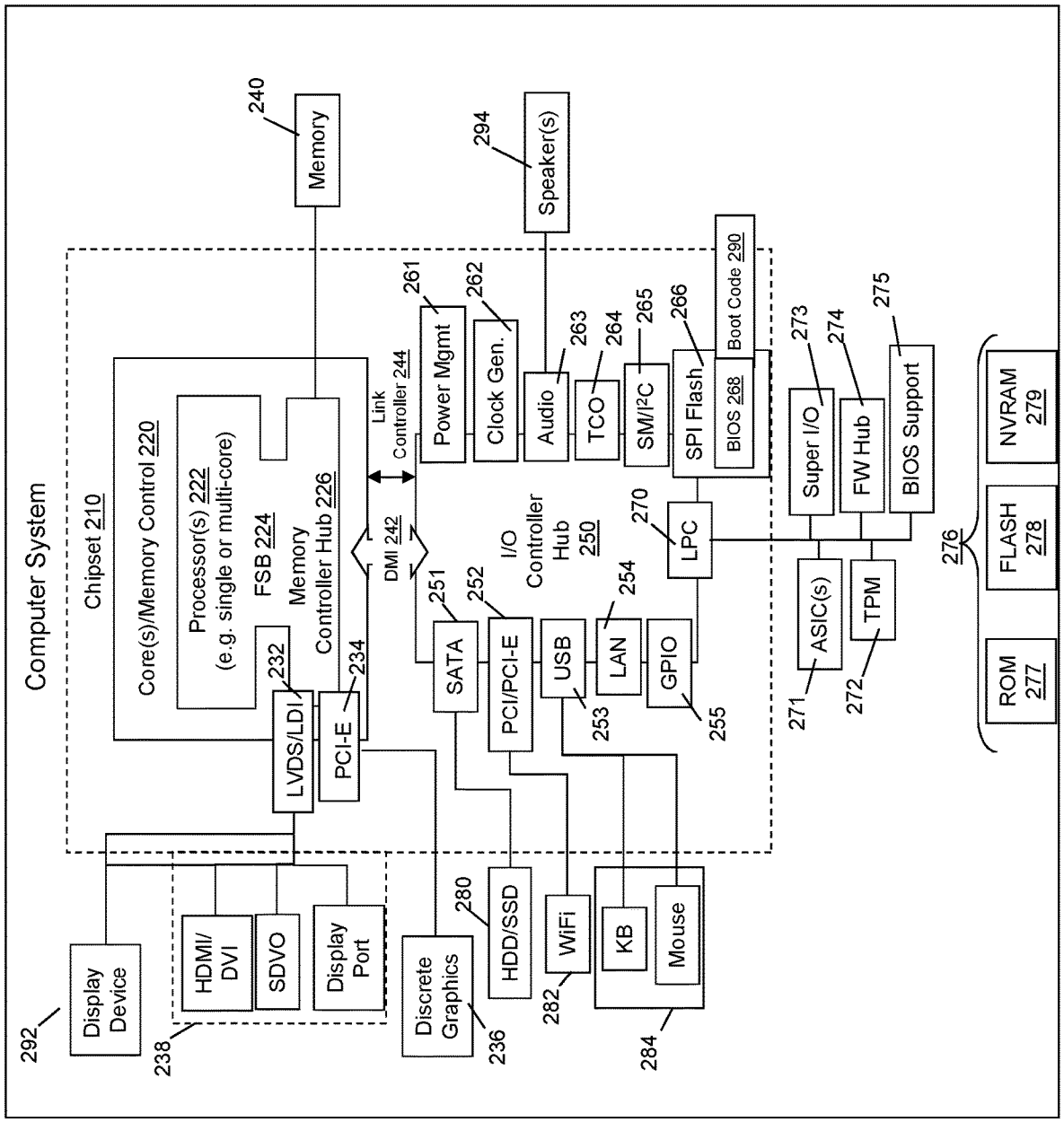
FIG. 2 illustrates another example of information handling device circuitry.

FIG. 2 depicts a block diagram of another example of information handling device circuits, circuitry or components. The example depicted in FIG. 2 may correspond to computing systems such as personal computers, or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of random-access memory (RAM) that may be referred to as "system memory" or "memory"). The memory controller hub 226 further includes a low voltage differential signaling (LVDS) interface 232 for a display device 292 (for example, a cathode-ray tube (CRT), a flat panel, touch screen, etc.). A block 238 includes some technologies that may be supported via the low-voltage differential signaling (LVDS) interface 232 (for example, serial digital video, high-definition multimedia interface/digital visual interface (HDMI/DVI), display port). The memory controller hub 226 also includes a PCI-express interface (PCI-E) 234 that may support discrete graphics 236.

In FIG. 2, the I/O hub controller 250 includes a SATA interface 251 (for example, for hard-disc drives (HDDs), solid-state drives (SSDs), etc., 280), a PCI-E interface 252 (for example, for wireless connections 282), a universal serial bus (USB) interface 253 (for example, for devices 284 such as a digitizer, keyboard, mice, cameras, phones, microphones, storage, other connected devices, etc.), a network interface 254 (for example, local area network (LAN)), a general purpose I/O (GPIO) interface 255, a LPC interface 270 (for application-specific integrated circuit (ASICs) 271, a trusted platform module (TPM) 272, a super I/O 273, a firmware hub 274, BIOS support 275 as well as various types of memory 276 such as read-only memory (ROM) 277, Flash 278, and non-volatile RAM (NVRAM) 279), a power management interface 261, a clock generator interface 262, an audio interface 263 (for example, for speakers 294), a time controlled operations (TCO) interface 264, a system management bus interface 265, and serial peripheral interface (SPI) Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as tablets, smart phones, personal computer devices generally, and/or electronic devices, which may be used in systems that analyze images and/or identify a condition of a portion of a user from images. For example, the circuitry outlined in FIG. 1 may be implemented in a tablet or smart phone embodiment, whereas the circuitry outlined in FIG. 2 may be implemented in a personal computer embodiment.

Figure 3:
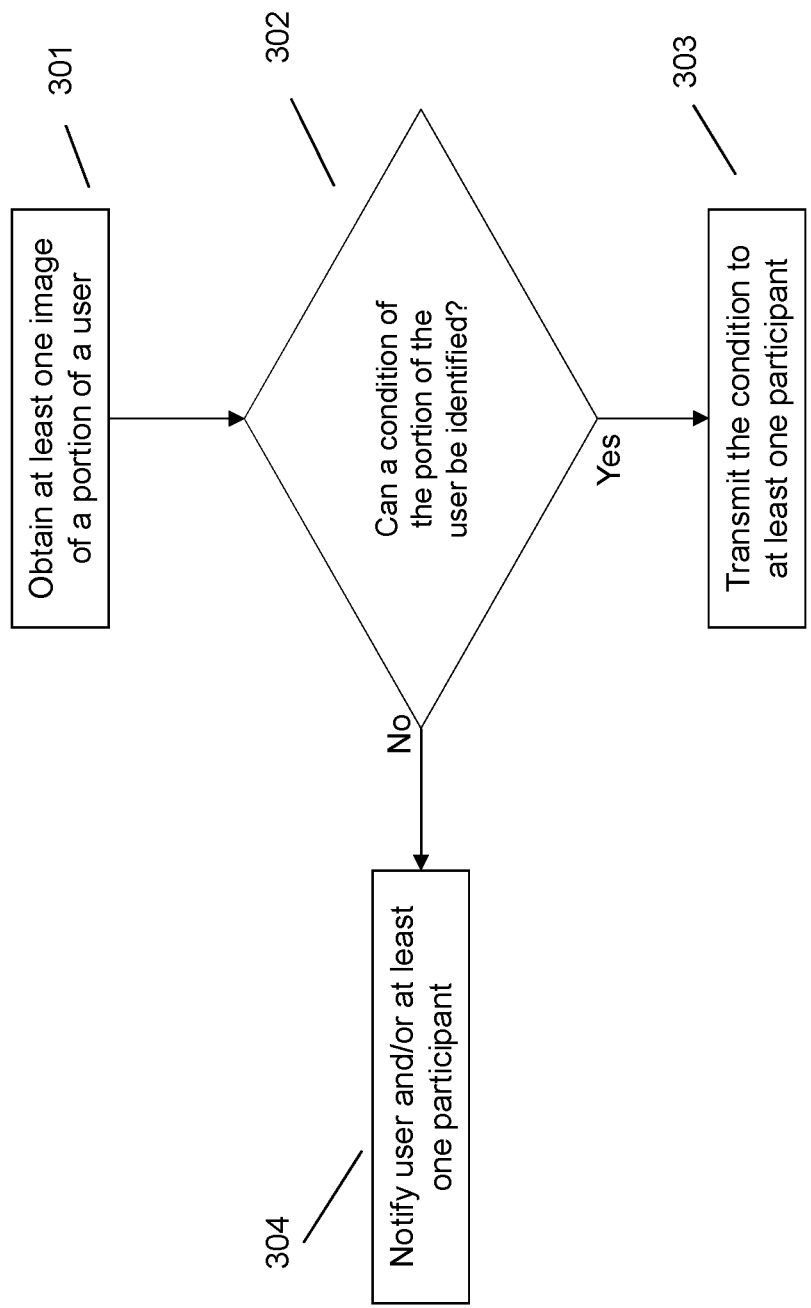
FIG. 3 illustrates an example method for identifying a condition of a portion of a user from images captured by an information handling device and transmitting the condition to a remote participant.

FIG. 3 illustrates an example method for identifying a condition of a portion of a user from images captured by an information handling device and transmitting the condition to a remote participant. The method may be implemented on a system which includes a processor, memory device, output devices (e.g., display device, printer, etc.), input devices (e.g., keyboard, touch screen, mouse, microphones, sensors, biometric scanners, etc.), image capture devices, and/or other components, for example, those discussed in connection with FIG. 1 and/or FIG. 2. While the system may include known hardware and software components and/or hardware and software components developed in the future, the system itself is specifically programmed to perform the functions as described herein to identify a condition of a user from images captured using an information handling device of a user. Additionally, the image diagnosis system includes modules and features that are unique to the described system.

The image diagnosis system may be implemented on a single information handling device or a system of devices. Generally, the information handling device utilized by the user to conduct or facilitate the video conference will be a traditional user device, for example, smart phone, cellular phone, laptop computer, smart watch, tablet, and/or other user devices that have the ability to capture and/or transmit images and/or videos. Thus, this information handling device may include the image diagnosis system or have access to the image diagnosis system. For example, the image diagnosis system may be located on a network location, for example, cloud network location, remote network location, local network locations, and/or the like, and accessible to the information handling device. Additionally, or alternatively, different portions of the image diagnosis system may be stored or located across different devices, data storage locations, and/or systems. For example, one module of the system may be stored on the user device of the user and one module of the system may be stored in a cloud storage location. Thus, the use of the term information handling device and/or image diagnosis system may refer to a single device or a system of devices.

The image diagnosis system may run in the background of an information handling device and may be activated when the device is activated. Additionally, or alternatively, the system may be activated when a video conference application is activated, detected, or otherwise opened. The user may also provide input indicating that the system should be activated. In this case, the system will not be activated until the user input is received. The system may also be activated upon detection of one or more conditions. For example, a user may not want the system to be activated for every video conference and may, instead, only want the system to be activated when a video conference with a medical professional is activated, when a video conference with a particular or particular type of medical professional is activated, and/or the like. Thus, the system may identify one or more conditions have been met and thereafter activate the image diagnosis system. For example, the system may detect that a video conference with a particular medical professional has been activated and thereafter activate the system.

The image diagnosis system may also be integrated into or activated by an application corresponding to a medical professional, medical entity, insurance entity, and/or the like. For example, many telemedicine visits (e.g., video conferences conducted with a medical professional) are conducted using a video conference system or application associated with the medical provider, medical professional, medical entity, and/or the like. This is done for various reasons including ensuring privacy, preventing recordings, ensuring a consistent format for the medical professionals, and/or the like. Thus, the image diagnosis system may be integrated into this application. This would also ensure that recordings or still images could be captured during the video conference. However, the use of a medical associated application is not required as other techniques for allowing capturing of video recordings or image captures are possible using other applications, for example, through the authorization of participants, upon request by one or more of the participants, consent of the participants, and/or the like.

At 301 the image diagnosis system may obtain at least one image of a portion of a user. As previously noted, the at least one image will be obtained using an information handling device of a user and that is facilitating a video conference with at least one remote participant. Facilitating means conducting, engaging within, or otherwise participating in a video conference. A remote participant is one who is not physically located in the same environment or space as the user of the information handling device. In the example of the telemedicine or medical appointment, the remote participant would likely be the medical professional.

It should be noted that the information handling device itself may not capture the image, but may instead provide instructions to capture the image. For example, if the user is using a smart phone to participate in the video conference but has access to other devices that have image capture devices or sensors, for example, a smart watch, laptop, tablet, and/or the like, the smart phone may provide instructions to one of these operatively coupled devices to capture the image, which is then transmitted to the information handling device. This may be particularly useful if different devices have different image sensors and, therefore, the ability to capture different types of images. However, it should be noted that a single device may include all of the desired or necessary image sensors to capture the desired images and image types.

A portion of the user may be a portion of the user that is of interest to the user and/or remote participant. The example of skin conditions will be used here throughout. However, this is merely a non-limiting example, as the described image diagnosis system can be used for other conditions. For example, the described system can be used for eye conditions, bruising, and/or other medical conditions. Using the skin condition example, the portion of the user may be the portion of the user that includes the skin condition or area of interest that the user wants to be analyzed. In order to gather as much information from the image as possible, the system may obtain more than one type of image. For example, the system may obtain a traditional color image using a red-green-blue (RGB) image sensor. This type of image sensor is the type of image sensor that is included in traditional user devices and is typically used to capture most images by the device. This may also be referred to as visible light imaging.

The system may also obtain a near infrared image using a near infrared image sensor. Many user devices also include near infrared image sensors. Near infrared images capture additional details that are unable to be captured using visible light imaging. Thus, the use of an infrared image provides additional or different information regarding a portion of the user than a traditional color image. When used together, the color image and the infrared image can be used to identify more details about the portion of the user than compared to utilizing a single one of the images. Therefore, when an image is captured or obtained, multiple images may be obtained to provide greater detail regarding the portion of the user. The images may be captured or obtained simultaneously or may be captured or obtained at different times. While the examples of a color and infrared image are utilized, different image types may be utilized and may provide additional or different information than that described herein.

Obtaining an image may be performed automatically. For example, the system may identify a condition that would indicate an image needs to be taken. Such a condition may include detecting a particular portion of interest, the information handling device being held in a particular location for a period of time, and/or the like. Obtaining an image may be performed responsive to receiving a user input indicating that an image should be obtained. For example, a user may provide touch input to a button or icon on the device, may say a particular word or phrase, may perform a particular gesture, and/or the like, to indicate that an image should be obtained. Obtaining an image may not require a separate image capture from the ongoing or continuous video capture. Rather, obtaining the image may include parsing the video to create a still image or series of images. In other words, rather than taking a separate image capture, the system may simply parse the video and extract the frames from the video that correspond to the time of the desired image. Alternatively, or additionally, obtaining the image may include taking a separate image capture. In other words, while the video is ongoing, the system may also activate an image capture mode and capture an image separate from the video capture.

At 302, the image diagnosis system attempts to identify a condition of the portion of the user by analyzing the image (s) of the portion of the user. Different characteristics of the portion of the user can be identified from the image(s). For example, different colors of the portion of the user, a size of the portion of the user, a shape of the portion of the user, and/or the like. Depending on the types of images that are obtained, different characteristics may be identified or different qualities of characteristics can be identified. For example, if an infrared image is obtained, a spectral reflectance of the near infrared image can be measured which can provide different depth information as compared to a color image, can provide different color or sizing information as compared to a color image, and/or the like. Thus, identifying the condition may include augmenting information from one image with information obtained from another image. For example, the identifying may include augmenting the information obtained from the color image with the information obtained from the near infrared image.

If more than one image sensor is utilized to obtain images, for example, an RGB image sensor and a near infrared image sensor, additional characteristics of the portion of the user may be able to be identified. For example, if the image sensors are located on one device, the images sensors will be separate from each other. This also means there is a spatial difference between the two image sensors. Thus, there is a spatial disparity between the sensors which can result in a depth signature for the portion of the user which can be used in identifying the condition.

From the identified characteristics, the image diagnosis system can identify a condition of the portion of the user. As a non-limiting example, the condition may be a medical condition. The system may compare the identified characteristics to characteristics of known conditions to identify the condition. To identify the condition, the image diagnosis system may utilize a neural network, machine-learning model, and/or other learning algorithm, collectively referred to as a neural network for ease of readability. The neural network can be trained utilizing image data that has been previously classified with conditions. In other words, the neural network is given annotated images that identify a condition associated with the image. These annotated images are referred to as a training dataset. The training dataset includes many different images and condition classifications corresponding to the images.

Using the training dataset, which may change over time, the neural network learns nuances between images that result in a particular condition. For example, different colors, sizes, shapes, depth signatures, and other characteristics of portions of users may be indicative of different conditions. The trained neural network can then be used to predict or infer conditions from non-annotated images, or new images. As conditions are predicted for new images and the prediction is confirmed or modified, the neural network can learn additional nuances and become more accurate and refined over time. Thus, while there is an initial training dataset that is used to initially train the neural network, the neural network is learning over time based upon new information received by the neural network, thereby ever evolving to come more accurate. The condition identified by the system may be a specific condition or may be a class of conditions.

Using the skin example, a specific condition may be specific type of skin cancer, whereas a class of conditions may simply be skin cancer.

If the image diagnosis system cannot identify a condition of the portion of the user at 302, the system may notify the user and/or the remote participant at 304. The notification may include instructing the user to obtain another image, move the information handling device to a different position, and/or the like. Even if a condition cannot be identified by the image diagnosis system, the system may transmit the image(s) to the remote participant, or medical professional, to be manually analyzed or analyzed using other devices. If a condition can later be identified, this information may be fed back to the image diagnosis system as feedback, either manually or automatically. This feedback can be used by the system to automatically retrain the neural network to make it more accurate.

If, on the other hand, the image diagnosis system can identify a condition of the portion of the user at 302, the system may transmit the condition to at least one participant. The condition may only be transmitted to the remote participant, or medical professional, and not transmitted to the user. This may ensure that inaccurate condition predictions are not provided to the user. Additionally, a medical professional may prefer to inform a patient of a condition as opposed to letting a machine provide a diagnosis.

The remote participant may also independently analyze the image(s) and come to a conclusion about the condition. The analysis of the remote participant can be captured by the image diagnosis system and used to make the system more accurate in identifying conditions, for example, by using the information as feedback to automatically retrain or enforce the neural network. A diagnosis by the remote participant that matches the condition identified by the system, reinforces the analysis that predicted the condition. A diagnosis by the remote participant that does not match the condition identified by the system, provides additional data points that make future analyses more accurate.

As an overall, non-limiting example, a user can conduct a video conference with a medical professional using a smart phone. As the user is participating in the video conference, the user can pan the smart phone over a portion of the user that is of interest to the user or medical professional. For example, if the user has a skin condition, the user can pan the smart phone over the skin condition so that not only can the medical professional see the skin condition in the video, but the information handling device can obtain an image of the skin condition. Once the image has been obtained, the image diagnosis system can analyze the image and attempt to identify the condition associated with the skin. For example, if the skin condition is melanoma, the system can attempt to identify the condition as melanoma. Once the system has identified the condition, the system transmits the condition to the medical professional. In this example, this means the system would transmits to the medical professional that the system has identified the condition as melanoma.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random-access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Additionally, the term "non-transitory" includes all media except signal media.

Program code embodied on a storage medium may be transmitted using any appropriate medium, including but not limited to wireless, wireline, optical fiber cable, radio frequency, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, the method comprising:
obtaining, using at least one sensor of an information handling device facilitating a video conference, at least one image of a portion of a user of the information handling device participating in the video conference, wherein at least one participant in the video conference is located remotely with respect to the user;
identifying, using an image diagnosis system, a condition of the portion of the user by analyzing the at least one image of the portion of the user; and
transmitting, using the image diagnosis system, the condition to the at least one participant.

2. The method of claim 1, wherein the obtaining at least one image comprises obtaining at least one color image and at least one near infrared image.

3. The method of claim 2, wherein the identifying comprises measuring a spectral reflectance of the at least one near infrared image.

4. The method of claim 2, wherein the identifying comprises augmenting information obtained from the at least one color image with information obtained from the at least one near infrared image.

5. The method of claim 1, wherein the identifying comprises utilizing a neural network.

6. The method of claim 5, wherein the neural network is trained utilizing image data previously classified with conditions.

7. The method of claim 1, wherein the identifying comprises identifying a depth signature associated with the at least one image.

8. The method of claim 1, wherein the identifying comprises determining a size of the portion of the user from the at least one image.

9. The method of claim 1, wherein the condition comprises a medical condition.

10. The method of claim 1, wherein the information handling device comprises a personal user device of the user.

11. A system, the system comprising:
an information handling device comprising at least one sensor;
a processor operatively coupled to the information handling device;
a memory device that stores instructions that, when executed by the processor, causes the system to:
obtain, using the at least one sensor of the information handling device that is facilitating a video conference, at least one image of a portion of a user of the information handling device participating in the video conference, wherein at least one participant in the video conference is located remotely with respect to the user;
identify, using an image diagnosis system, a condition of the portion of the user by analyzing the at least one image of the portion of the user; and
transmit, using the image diagnosis system, the condition to the at least one participant.

12. The system of claim 11, wherein the obtaining at least one image comprises obtaining at least one color image and at least one near infrared image.

13. The system of claim 12, wherein the identifying comprises measuring a spectral reflectance of the at least one near infrared image.

14. The system of claim 12, wherein the identifying comprises augmenting information obtained from the at least one color image with information obtained from the at least one near infrared image.

15. The system of claim 11, wherein the identifying comprises utilizing a neural network.

16. The system of claim 15, wherein the neural network is trained utilizing image data previously classified with conditions.

17. The system of claim 11, wherein the identifying comprises identifying a depth signature associated with the at least one image.

18. The system of claim 11, wherein the identifying comprises determining a size of the portion of the user from the at least one image.

19. The system of claim 11, wherein the information handling device comprises a personal user device of the user.

20. A product, the product comprising:
a computer-readable storage device that stores executable code that, when executed by a processor, causes the product to:
obtain, using at least one sensor of an information handling device facilitating a video conference, at least one image of a portion of a user of the information handling device participating in the video conference, wherein at least one participant in the video conference is located remotely with respect to the user;
identify, using an image diagnosis system, a condition of the portion of the user by analyzing the at least one image of the portion of the user; and
transmit, using the image diagnosis system, the condition to the at least one participant.

* * * * *